(12) United States Patent
Nickel

(10) Patent No.: US 9,903,929 B2
(45) Date of Patent: *Feb. 27, 2018

(54) METHOD AND APPARATUS FOR ACQUIRING MAGNETIC RESONANCE DATA AND GENERATING IMAGES THEREFROM USING A TWO-POINT DIXON TECHNIQUE

(71) Applicant: Siemens Aktiengesellschaft, Munich (DE)

(72) Inventor: Marcel Dominik Nickel, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 696 days.

This patent is subject to a terminal disclaimer.

(21) Appl. No.: 14/476,917

(22) Filed: Sep. 4, 2014

(65) Prior Publication Data

US 2015/0061667 A1    Mar. 5, 2015

(30) Foreign Application Priority Data

Sep. 4, 2013    (DE) .................. 10 2013 217 650

(51) Int. Cl.
*G01V 3/00* (2006.01)
*G01R 33/485* (2006.01)
(Continued)

(52) U.S. Cl.
CPC .......... *G01R 33/485* (2013.01); *A61B 5/055* (2013.01); *G01R 33/46* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 7,941,204 B1 *    5/2011  Wang ................ G01R 33/4824
                                             324/307
2004/0101184 A1 *  5/2004  Sivaramakrishna .. G06T 7/0012
                                             382/131
(Continued)

FOREIGN PATENT DOCUMENTS

WO    WO-2012038886 A1    3/2012
WO    WO-2013001415 A1    1/2013

OTHER PUBLICATIONS

Hernando "Joint estimation of water and fat images from magnetic resonance signals"; Dissertation; University of Illinois; Urbana-Champaign (2015).

(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

Magnetic resonance (MR) data are acquired with a two-point Dixon technique in which a first spectral component and a second spectral component, for example, a water component and a fat component, are determined. A computation grid of lower resolution in comparison to the MR data is determined, wherein each grid point of the computation grid encompasses a predetermined number of adjacent image points of the MR data. A numerical optimization is implemented for each image point of the MR data, and the first spectral component and the second spectral component are calculated analytically based on the result of the numerical optimization.

20 Claims, 6 Drawing Sheets

(51) Int. Cl.
*A61B 5/055* (2006.01)
*G01R 33/46* (2006.01)
*G01R 33/48* (2006.01)
*G01R 33/565* (2006.01)

(52) U.S. Cl.
CPC .... *G01R 33/4828* (2013.01); *G01R 33/56518* (2013.01); *G01R 33/56563* (2013.01)

(58) Field of Classification Search
USPC .......................................................... 324/307
See application file for complete search history.

(56) References Cited

U.S. PATENT DOCUMENTS

| | | | |
|---|---|---|---|
| 2007/0035302 A1* | 2/2007 | Ikedo | G01R 33/56563 324/320 |
| 2010/0014730 A1* | 1/2010 | Hahn | G06T 5/50 382/131 |
| 2011/0267054 A1* | 11/2011 | He | A61B 5/055 324/309 |
| 2012/0008847 A1 | 1/2012 | Brendel et al. | |
| 2012/0224757 A1 | 9/2012 | Gross | |
| 2012/0316795 A1* | 12/2012 | Eggers | G01N 24/08 702/22 |

OTHER PUBLICATIONS

Berglund et al.,; "Two-point Dixon Method With Flexible Echo Times", ; Magnetic Resonance in Medicine, vol. 65, (2011) pp. 994-1004.

Eggers et al.; "Dual-Echo Dixon Imaging with Flexible Choice of Echo Times", Magnetic Resonance in Medicine, vol. 65, (2011) pp. 96-107.

Yu et al., "Field Map Estimation with a Region Growing Scheme for Iterative 3-Point Water-Fat Decomposition," Magnetic Resonance in Medicine, vol. 54, (2005) pp. 1032-1039.

Golub et al., "The Differentiation of Pseudo-Inverses and Nonlinear Least Squares Problems Whose Variables Separate," SIAM Journal of Numer. Anal., vol. 10, No. 2 (1973), pp. 413-432.

* cited by examiner

FIG 5
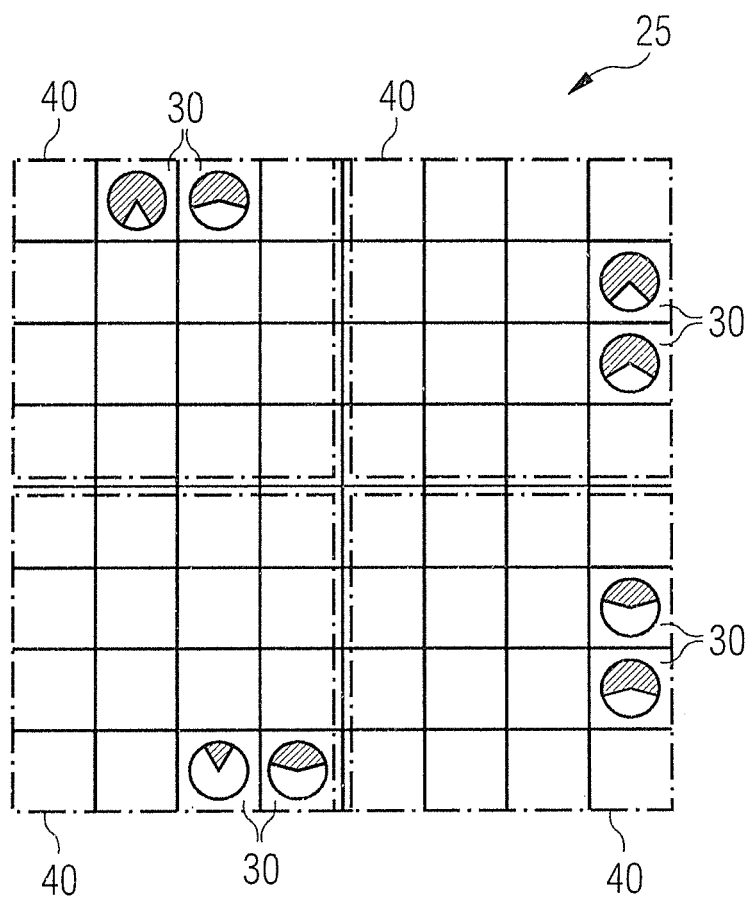
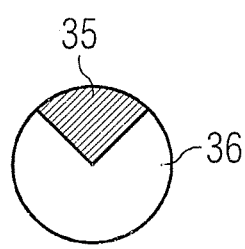

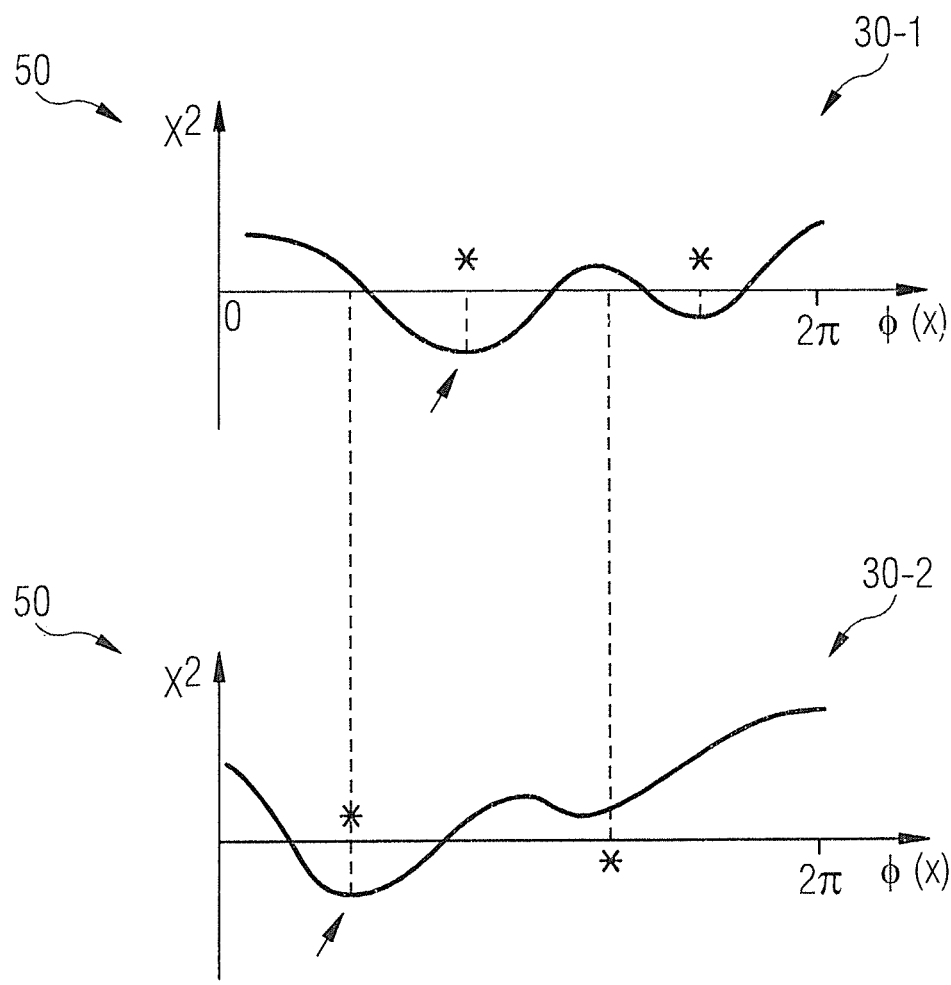

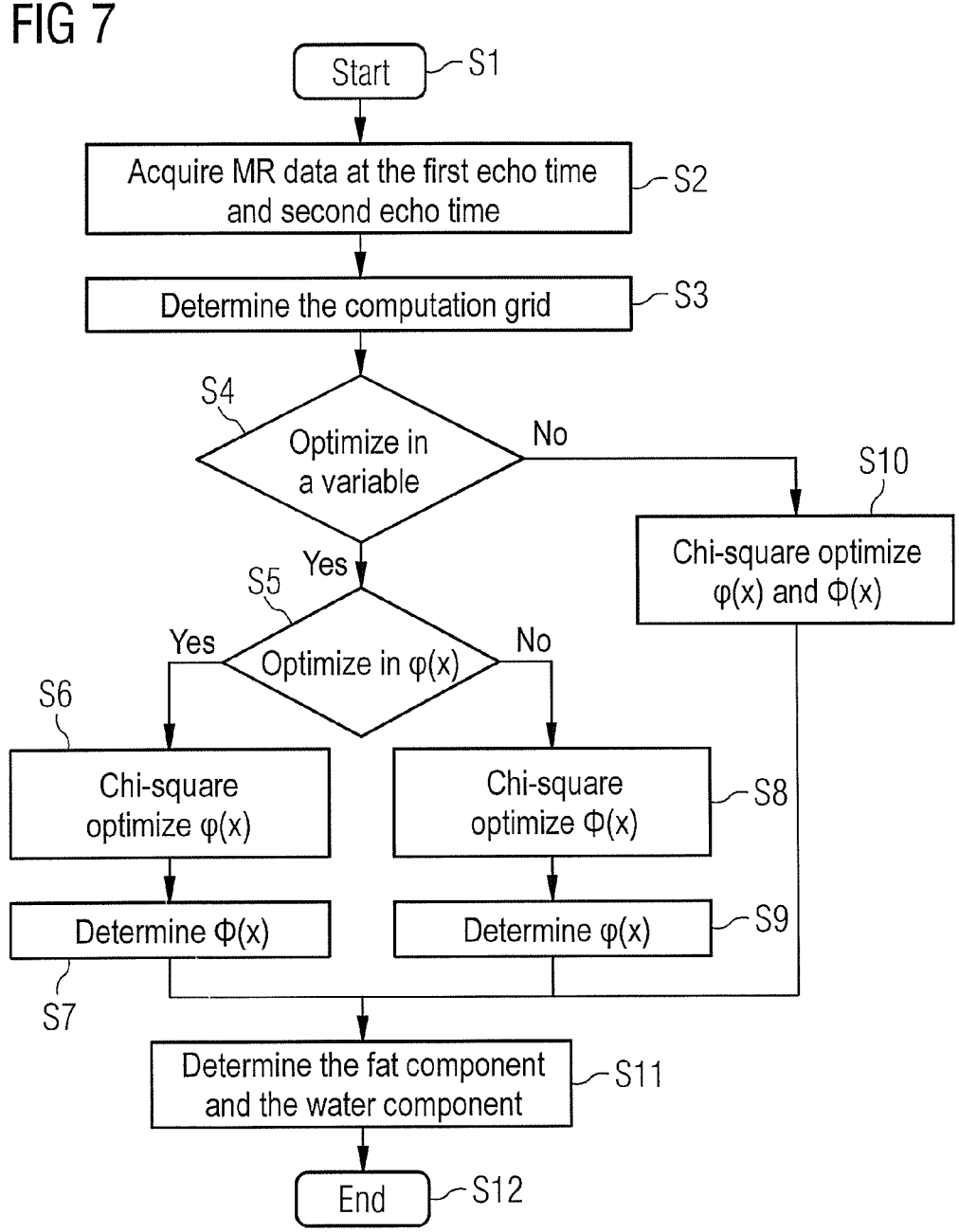

METHOD AND APPARATUS FOR ACQUIRING MAGNETIC RESONANCE DATA AND GENERATING IMAGES THEREFROM USING A TWO-POINT DIXON TECHNIQUE

BACKGROUND OF THE INVENTION

Field of the Invention

The invention concerns a method for magnetic resonance (MR) measurement and a magnetic resonance system. In particular, the invention concerns techniques by means of which a determination of first and second spectral components from MR data is possible.

Description of the Prior Art

In the acquisition of magnetic resonance data, it is possible to separate spectral components that are included in the MR data. The spectral components can designate different spin species, for example nuclear spins in an adipose environment and in an aqueous environment. For this purpose, what are known as chemical shift imaging multi-echo magnetic resonance measurement sequences are often used within the scope of Dixon techniques. Such techniques typically utilize the effect that the resonance frequency of nuclear spins depends on the molecular or chemical environment. This effect is designated as a chemical shift. Different spin species therefore have different resonance frequencies from which the measured spectrum of the MR data is composed. For example, the difference between two resonance frequencies of different spectral components can be expressed in ppm ("parts per million", i.e. 106

The chemical shift between hydrogen nuclear spins in water as a first spectral component and hydrogen nuclear spins in fatty acid chains as a second spectral component is often utilized. In such a case, a water MR image and/or a fat MR image—i.e. individual MR images of the two spectral components—can be determined using MR data. This is of interest in a variety of applications, for example clinical and/or medical applications.

In order to be able to separate the spectral components from one another, MR signals are acquired at multiple echo times within the scope of the Dixon technique. The MR signals together form the MR data. The different spectral components have different phase positions at the different echo times. Using this effect, it is be possible to determine the different spectral components separately.

For this purpose, a spectral model is generally used that links the measured or acquired MR data with different physically relevant variables. The different variables include the different spectral components to be determined, as well as additional unknowns of the measurement system (depending on precision, scope and complexity of the spectral model). It can then be possible to determine the spectral components considered in the spectral model for each image point of the MR data.

In principle, it can be worthwhile to use a relatively complex spectral model, for example such a spectral model which considers a large number of further unknowns in addition to the spectral components to be determined. It can then be possible to determine the spectral components particularly precisely. In this case, however, it can be necessary to acquire particularly many MR signals at different echo times, which can in turn extend a measurement duration and therefore can be disadvantageous. A trade-off situation thus often results between the measurement duration and the precision in the determination of the spectral components.

A need therefore exists for techniques that enable a relatively precise determination of spectral components, while simultaneously requiring only a small number of MR signals at different echo times, thus ensure a relatively short measurement duration.

In order to satisfy this requirement, techniques are known in which a numerical optimization enables the discovery of solutions to an equation (which forms the basis of the spectral model that is used) to determine the spectral components. However, since the spectral models of the two spectral components can be very similar, the underlying equations can be nearly symmetrical in the spectral components. Therefore, in such scenarios a situation can also occur in which multiple solutions are discovered and it is not clear (or it is clear only to a limited extent) which of the multiple solutions is the physically relevant solution. In other words: the equation underlying the spectral model cannot be uniquely solved.

In order to remedy this ambiguity in the determination of the spectral components, it is to take that various variables into account in the spectral model are assumed to be only slightly dependent on position. For example, a variable that describes the field inhomogeneities of a basic magnetic field of an MR system that is used can be assumed to be relatively slightly dependent on position. A relatively slight dependency on position can in particular mean: only a small change on the length scale of an image point of the MR data. An image point of the MR data can have a size of 1 mm×1 mm×1 mm, for example. This size of the image point typically determines the spatial resolution of the final MR image, i.e. in particular the resolution with which the first and second spectral components are determined. Another factor, however, is that the basic magnetic field can exhibit inhomogeneities that vary only on an order of 1 cm or more, thus do not or do not significantly vary between two adjacent image points of the MR data.

In such a case, after the numerical discovery of the multiple solution candidates, one of these solution candidates can be chosen as the physically correct solution, and in fact depending on a solution already found beforehand for a neighboring image point. Such techniques are known to those skilled in the art, for instance under the name "region growing techniques".

Such techniques have limitations or disadvantages. The implementation of the numerical optimization thus can be computationally intensive.

SUMMARY OF THE INVENTION

A need therefore exists for techniques which enable an improved determination of spectral components from MR data. In particular, there is a need for such techniques that enable a particularly simple and less computationally intensive determination of the spectral components. A need also exists for such techniques that determine the spectral components with a relatively high precision.

According to one aspect of the invention, a method is provided for magnetic resonance measurement of a first spectral component and a second spectral component of an examination subject by using a two-point Dixon technique at a first echo time and a second echo time. The predetermined spectral model of the two-point Dixon technique includes the first spectral component, the second spectral component, a phase at the first echo time and a phase evolution due to field inhomogeneities and/or eddy current effects between the first echo time and the second echo time. The method includes the acquisition of MR data for multiple image points, respectively at the first echo time and at the second echo time. Furthermore, the method includes the determination of a computation grid of low resolution in comparison to the MR data, wherein each grid point of the computation grid encompasses a predetermined number of adjacent image points of the MR data. For each image point of the MR data, the method furthermore includes the implementation of a numerical optimization that determines an optimized phase at the first echo time and/or an optimized phase evolution. The optimization is based on an equation that takes into account that the phases at the first echo time and/or the phase evolution for all image points that are encompassed by a grid point of the computation grid is constant. The method furthermore includes the analytical calculation of the first spectral component and of the second spectral component based on the phase determined by the optimization at the first echo time and/or the phase evolution.

The resolution of the MR data can be determined by the variable of an image point of the MR data, for example as a number of image points per area. The MR data can be composed of an MR signal at the first echo time and an MR signal at the second echo time. The first and second echo time can typically be determined relative to a time period between an MR signal and a radiated radio-frequency (RF) excitation pulse. For example, the acquisition of the MR data can take place by means of a spin echo MR measurement sequence and/or by means of a gradient echo MR measurement sequence. Within the scope of the MR measurement sequence, two echoes can then be formed that correspond to the MR signals at the first and second echo time. The gradient echo MR measurement sequence can be bipolar or monopolar.

In other words, a grid point of the computation grid can designate that region within which the phases at the first echo time and/or the phase evolution are assumed to be constant in the numerical optimization, i.e. have a fixed value. The scale of a grid point of the computation grid can correlate with that length scale at which it is assumed that the phase at the first echo time and/or the phase evolution exhibit no significant change. For example, a grid point can be quadratic or rectangular, i.e. encompasses a different number of image points of the MR data along different spatial directions; more complex influences of varying unknowns that have spatial dependencies of different strengths for different spatial directions can therefore be taken into account. Merely as an example, a grid point of the computation grid can encompass 2×2 or 2×4 or 6×6 or 20×20 or 100×50 image points of the MR data. It would also be possible that the size of a grid point of the computation grid is different at various locations. For instance, more complex spatial dependencies of the field inhomogeneities and/or of the eddy current effects can therefore be considered. For example, the analytical calculation of the first and second spectral components can take place for each image point, but can also take place jointly for multiple image points.

In principle, the numerical optimization can be delimited compared to analytical techniques. For example, within the scope of the numerical optimization iterative techniques can be implemented, for example with regard to solutions of the equation. For example, it is possible that the numerical optimization yields multiple solutions of the equation as result candidates. Within the scope of the optimization, it can then be required that, for each image point, one solution is chosen from the multiple result candidates as the optimized phase at the first echo time, and/or the optimized phase evolution. However, it is also possible for the numerical optimization also include analytical calculation steps, for example in addition to the numerical techniques noted above.

As described above, within the scope of the discovery of solutions of the equation within the scope of the numerical optimization it can already be taken into account that the phase at the first echo time and/or the phase evolution is constant within a grid point of the computation grid. Stated differently, at the point in time of implementing the numerical optimization, it can thus already be taken into account that the phase at the first echo time and/or the phase evolution has a smaller dependency on position than the MR data themselves. In spite of that, the phase at the first echo time and/or the phase evolution can thus be assumed to be constant in parts in the numerical optimization.

An efficient and less computationally intensive numerical optimization is thereby achieved, particularly in comparison to reference implementations in which, only after the numerical optimization (in particular after the discovery of result candidates), is it taken into account that the phase at the first echo time and/or the phase evolution are constant in parts.

A precise determination of the first spectral component and of the second spectral component is thereby also achieved. This is because a higher signal-to-noise ratio of the phase images is achieved through the assumption that the phase at the first echo time and the phase evolution are constant in subsets within a grid point, and as a result of this a higher signal-to-noise ratio of the spectral components subsequently calculated based on these in the individual image points is also achieved. Within the scope of the numerical optimization, the signal-to-noise ratio can be increased since the data foundation on which the numerical optimization is implemented is increased via averaging over multiple MR signals.

In general, the numerical optimization can be implemented based on any optimization technique known in principle to those skilled in the art. For example, it is possible for the optimization to be a chi-square optimization or an Lp-norm optimization. For example, the optimization problems can be solved by the Marquardt-Levenberg method.

For example, the optimization can be implemented with regard to the phase at the first echo time or with regard to the phase evolution, or both with regard to the optimized phase and with regard to the phase evolution. In general, numerical optimization techniques are known that provide result candidates for one, two or more unknowns of the equation on which the numerical optimization is based. In general, the precision is greater (lesser) the fewer (more) unknowns that are determined within the scope of the numerical optimization.

In particular, the equation can have no explicit dependency on the first spectral component and the second spectral component. No explicit dependency means a partial derivation of the equation according to one of the first spectral component and the second spectral component yields zero.

The equation on which the optimization is based can be derived from the predetermined spectral model. In this regard, a number of techniques are known that allow the spectral model to be reformulated such that the equation has no explicit dependency on the first and second spectral components.

For the case that the equation has no explicit dependency on the first and second spectral components, the effect of a particularly simplified numerical optimization can be achieved. In such a case it can be unnecessary for the numerical optimization to yield direct result candidates for the first spectral component and/or the second spectral component. In other words: in such a case the numerical optimization only provides result candidates for the phase at the first echo time and/or the phase evolution. The optimization thus can inherently take into account the first and second spectral portion but without itself providing a direct solution for the first and spectral portions. In general, the computing resources necessary to implement the numerical optimization are greater (lesser) for a larger (smaller) number of variables to be optimized.

The predetermined spectral model can assume real-value weightings for the first and second spectral components. Alternatively, the predetermined spectral model can assume complex-valued weightings, i.e. in other words additional weightings associated with a phase for the two spectral components. For the latter case, it is possible that the phase at the first echo time to be expressed by the complex-valued weightings of the first and second spectral components.

For example, the equation can be described by a variable projection of real-value weightings of the two spectral components on the basis of the spectral model. If the spectral model is based on the real-value weightings for the two spectral components, a particularly simple elimination of explicit dependencies on the phase at the first echo time and/or the phase evolution can take place.

The determination of the computation grid can furthermore encompass the establishment of the predetermined number of adjacent image points of the MR data that are encompassed by a grid point, depending on a user input and/depending on a machine parameter of a magnetic resonance system.

In other words: the determination of the computation grid can furthermore encompass the establishment of a dimension of a grid point of the computation grid depending on the user input and/or the machine parameter. If a larger (smaller) number of adjacent image points of the MR data that are encompassed by a grid point of the computation grid is established, in general the implementation of the numerical optimization can require lesser (greater) computing capacities. In general, defined computation operations within the scope of the numerical optimization can be implemented simultaneously and without differentiation for all of those adjacent image points of the MR data that are encompassed by a grid point of the computation grid. Therefore, given a larger (smaller) number of image points of the MR data that are encompassed by a grid point of the computation grid, the number of computation operations within the scope of the numerical optimization can be reduced (increased). At the same time, a maximized precision can be achieved for a defined number of image points that are encompassed by a grid point. Namely, the signal-to-noise ratio can be increased by the averaging (described in the preceding) of the MR signals of multiple image points within the scope of the numerical optimization. At the same time, given grid points of the computation grid that are chosen to be too large, the spatial dependency of the phase at the first echo time and/or the spatial dependency of the phase evolution can no longer be sufficiently precisely described. Therefore, an optimum of the size of the grid points can be provided which can be determined depending on machine parameters, for example. The optimum can take into account precision and computing capacities.

For example, the machine parameters can be selected from a group that includes the following values: quality of a basic magnetic field of the magnetic resonance system; quality of a shielding from eddy current effects of the MR system; computing capacity of a computer of the MR system; size of an image point of the MR data; and/or strength of gradient fields of the MR system etc. All such machine parameters can have an influence on a change of field inhomogeneities and/or of eddy current effects as a function of the location.

For the case that only the phase evolution is numerically optimized, the equation can take into account that the phase at the first echo time varies for image points that are encompassed by a grid point of the computation grid. For the case that only the phase is numerically optimized at the first echo time, the equation can take into account that the phase evolution varies for image points that are encompassed by a grid point of the computation grid.

In other words, if the numerical optimization is implemented only with regard to either the phase at the first echo time or with regard to the phase evolution, the respective variable that is not considered is assumed to be variable within a grid point of the computation grid.

In such a technique, a particularly high precision can be achieved in the determination of the optimized phase at the first echo time and the determination of the optimized phase evolution. At the same time, however, it can be necessary to occupy increased computing capacity to implement the numerical optimization.

The calculation of the first and second components can furthermore include the interpolation of the phase at the first echo time and/or of the phase evolution between adjacent grid points of the computation grid. The determination of the first and second spectral components can be based on the interpolated phase at the first echo time and/or the interpolated phase evolution.

By means of such described techniques, the phase at the first echo time and/or the phase evolution can be assumed to be constant within a grid point of the computation grid. In contrast to this, the analytical calculation of the first spectral component and of the second spectral component for each image point of the MR data can be implemented separately within the scope of the method. The first and second spectral components therefore can be provided with a resolution that corresponds to that of the acquired MR data. For example, if a water MR image and a fat MR image are created on the basis of the defined first and second components, this high resolution of the water MR image and of the fat MR image can be worthwhile for a subsequent clinical or medical application. Therefore, it can be worthwhile to also allow a certain variation of the phases at the first echo time and/or of the phase evolution within a grid point of the computation grid by the interpolation after the implementation of the optimization. The first spectral component and the second spectral component thus can be calculated with a higher precision. At the same time, the interpolation can be a less computationally intensive operation, such that the necessary computing capacities are not significantly increased by this interpolation. Only physical changes of the phase at the first echo time and/or of the phase evolution that are of subordinate relevance, are sudden or that occur in stages can therefore be reduced. In other words, conditional artifacts can be reduced in the technique to determine the first and second spectral components.

According to a further aspect, the invention concerns a method for MR measurement of a first spectral component and a second spectral component of an examination subject by means of a two-point Dixon technique at a first echo time and a second echo time. A predetermined spectral model of the two-point Dixon technique includes the first spectral component, the second spectral component, a phase at the first echo time and a phase evolution due to field inhomogeneities and/or eddy current effects between the first echo time and the second echo time. The method includes the acquisition of MR data for multiple image points, respectively at the first echo time and at the second echo time. For each image point of the MR data, the method furthermore includes the implementation of a numerical optimization that determines an optimized phase at the first echo time and/or an optimized phase evolution. The optimization can be based on an equation that has no explicit dependency on the first and second spectral components. The method also includes the analytical calculation of the first spectral component and of the second spectral component based on the phase determined by the optimization at the first echo time and/or on the determined phase evolution.

For the method for MR measurement according to this aspect, corresponding techniques can be used as described above with regard to the method for MR measurement according to a further aspect of the present invention. For such techniques in which the numerical optimization is based on an equation without explicit dependency on the first and second spectral components, results can be achieved as explained above.

As described above, it is possible to implement the numerical optimization both with regard to the phase at the first echo time and with regard to the phase evolution, but it is also possible to implement the numerical optimization only with regard to either the phases at the first echo time or the phase evolution.

If only the phase evolution is numerically optimized, the equation can have no explicit dependency on the phase at the first echo time. Accordingly, if only the phase at the first echo time is numerically optimized, the equation can have no explicit dependency on the phase evolution.

In other words, it is possible for the equation to be based on the spectral model and, in addition to the elimination of the explicit dependency on the first and second spectral components for the explicit dependency on either the phase evolution or the phase at the first echo time to be eliminated.

A particularly simple and less computationally intensive numerical optimization is thereby achieved. The numerical optimization can be implemented only with regard to one of the phase evolution and the phase at the first echo time, and he other can be obtained by analytical calculation based on the optimized variable, for example. The precision can also be increased because, in the numerical optimization, the respective explicitly eliminated phase or phase evolution is inherently and precisely taken into account, and is not adulterated by the possibly limited precision of the numerical optimization.

The analytical calculation of the first spectral component and the second spectral component can occur based on a formula that is based on a variable back-projection of real-value weightings of the first and second spectral components.

If the explicit dependency at the first and second spectral components is eliminated from the spectral model by the variable projection, the analytical calculation of this elimination can be taken into account and in general represent an inverse calculation operation. The analytical calculation of the first and second spectral components can be less computationally intensive and be implemented quickly and particularly precisely.

In general, techniques of variable projection are known to those skilled in the art, for example from the article by G. H. Golub and V. Pereyra, "The differentiation of pseudoinverses and nonlinear least squares problems whose variables separate" in SIAM J. Numer. Anal. 10 (1973), 413-432. Therefore, there is no need to present additional details at this point with regard to the variable projection need not be presented herein.

As noted above, the implementation of the numerical optimization can provide multiple result candidates for an image point. The optimization can furthermore include the implementation of a region growing technique for the multiple image points of the MR data and, for each image point, with value then being selected from the multiple result candidates a value as the optimized phase at the first echo time and/or the optimized phase evolution. In general, the region growing technique can take into account results of the numerical optimization for adjacent image points of the MR data, i.e. for respective adjacent image points, the respective optimized phase at the first echo time and/or the optimized phase evolution is selected based on an initial image point. Suitable techniques are known in principle to the those skilled in the art, for example from H. Yu et al. "Field map estimation with a region growing scheme for iterative 3-point water-fat-decomposition" in Mag. Reson. Met. 54 (2005), 1032-1039. Therefore, further explanation of the region growing technique is not necessary herein.

According to a further aspect, the invention concerns an MR system that is designed for MR measurement of a first spectral component and a second spectral component of an examination subject, using a two-point Dixon technique, at a first echo time and a second echo time. A predetermined spectral model of the two-point Dixon technique includes the first spectral component, the second spectral component, a phase at the first echo time, and a phase evolution due to field inhomogeneities and/or eddy current effects between the first echo time and the second echo time. The MR system has an acquisition unit and a computer. The acquisition unit is designed in order to acquire MR data for multiple image points, respectively at the first echo time and at the second echo time. The computer is designed in order to determine a computation grid that is of low resolution in comparison to the MR data, wherein each grid point of the computation grid encompasses a predetermined number of adjacent image points. The computer is furthermore configured to implement a numerical optimization for each image point of the MR data, the numerical optimization determining an optimized phase at the first echo time and/or an optimized phase evolution. The optimization is based on an equation that takes into account that the phase at the first echo time and/or the phase evolution is constant for all image points that are encompassed by a grid point of the computation grid. The computer is furthermore configured to analytically calculate the first spectral component and the second spectral component based on the phase at the first echo time as determined by the optimization and/or based on the phase evolution determined by the optimization.

According to a further aspect, the invention concerns an MR system that is designed for MR measurement of a first spectral component and a second spectral component of an examination subject, with a two-point Dixon technique, at a first echo time and a second echo time. A predetermined spectral model of the two-point Dixon technique includes the first spectral component, the second spectral component, a phase at the first echo time, and a phase evolution due to field inhomogeneities and/or eddy current effects between the first echo time and the second echo time. The MR system has an acquisition unit and a computer. The acquisition unit is designed in order to acquire MR data for multiple image points, respectively at the first echo time and at the second echo time. The computer is designed in order to implement a numerical optimization for each image point of the MR data, which numerical optimization determines an optimized phase at the first echo time and/or an optimized phase evolution. The optimization is based on an equation that has no explicit dependency on the first and second spectral components. The computer is furthermore configured to analytically calculate the first spectral component and the second spectral component based on the phase at the first echo time as determined by the optimization and/or based on the phase evolution determined by the optimization.

The MR system is designed in order to implement the method according to the present invention.

MR systems according to the invention achieve results and advantages that are comparable to those achieved with methods according to the invention.

The features presented above and features that are described in the following can be used not only in the corresponding explicitly presented combinations, but also in additional combinations or in isolation, without departing from the scope of the invention.

BRIEF DESCRIPTION OF THE DRAWINGS

FIG. 5 schematically shows image points of the MR data, grid points of a computation grid, and first and second spectral components for the different image points.

FIG. 6 illustrates numerical optimization for two image points.

FIG. 7 is a flowchart of the method of the invention according to various embodiments.

DESCRIPTION OF THE PREFERRED EMBODIMENTS

Figure 1:
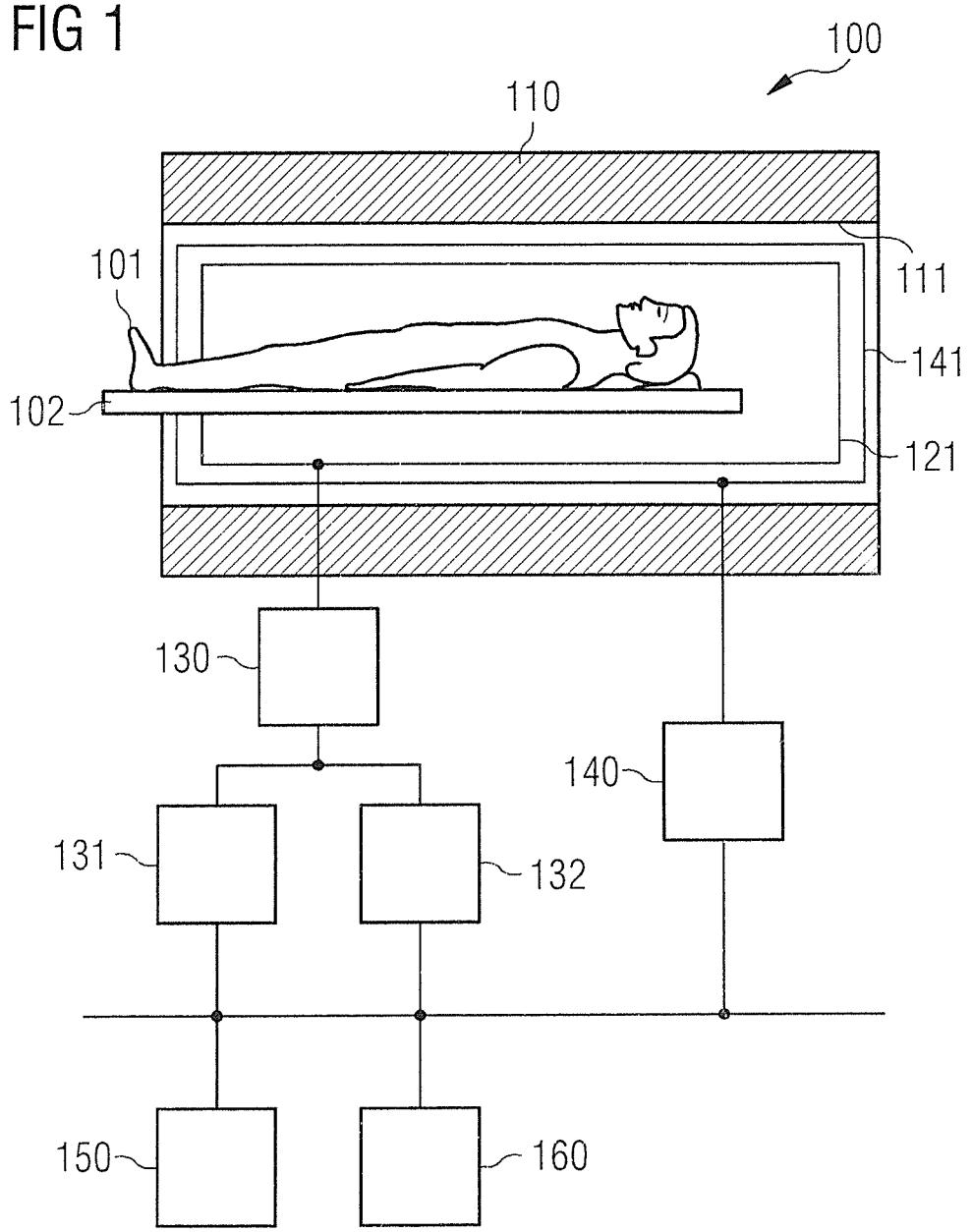
FIG. 1 schematically illustrates an MR system.

In the following, the present invention is explained in detail using preferred embodiments with reference to the drawings. In the figures, identical reference characters designate identical or similar elements. The subsequent description of embodiments with reference to the figures should not be construed as limiting. The figures are only illustrative.

The figures are schematic representations of different embodiments of the invention. Components shown in the figures are not necessarily true to scale. Rather, the different components presented in the figures are rendered such that their function and general purpose are comprehensible to those skilled in the art. Connections and couplings between functional units and elements that are depicted in the figures can also be implemented as indirect connections or couplings. A connection or coupling can be implemented via wires or wirelessly. Functional units can be implemented as hardware, software or a combination of hardware and software.

In the following, techniques are presented by which a first spectral component and a second spectral component can be determined from MR data. For example, the first spectral component can indicate a fat content (shortened to fat in the following) and the second spectral component can indicate a water content (shortened to water in the following). In general, however, any spin species—thus also silicone, for instance—can be considered as a first and second spectral component.

The MR data are acquired with a two-point Dixon technique, and thus include a first MR signal and a second MR signal, respectively at first and second echo times. A spectral model is also used that, in addition to the fat component and water component, also takes into account a phase at the first echo time and a phase evolution between the first and second echo times. Weightings of the fat component and of the water component that are used in the spectral model are typically assumed to have real values.

Within the scope of the spectral model, the first MR signal and the second MR signal $S_0(x)$, $S_1(x)$ can be expressed as $$S_0(x)=(W(x)+c_0 F(x))e^{i\varphi(x)}$$

$$S_1(x)=(W(x)+c_1 F(x))e^{i\varphi(x)+\phi(x)}, \quad (1)$$

where $W(x)$ and $F(x)$ are real-value water and fat components in an image point x of the MR data; $c_0$ and $c_1$ model the time dependency of fat and are known in principle and physically dependent on a spectral composition of the fat and the echo times themselves; $\varphi(x)$ is the phase at the first echo time and $\phi(x)$ is the phase evolution between the first and second echo time. The phase evolution $\phi(x)$ has its physical cause in field inhomogeneities of a basic magnetic field of the MR system and in eddy currents.

As noted above, a spectral model corresponding to Equation (1) can also be directly set up for other species than fat and water, but for simplicity only water and fat are referred to for the purposes of better illustration.

Equation (1) can also be depicted schematically:

$$S(x)=\Phi(x) A v(x), \quad (2)$$

wherein $$S(x) = \begin{pmatrix} S_0(x) \\ S_1(x) \end{pmatrix}, \Phi(x) = \begin{pmatrix} e^{i\varphi(x)} & \\ & e^{i(\varphi(x)+\phi(x))} \end{pmatrix} \quad (3)$$

$$A = \begin{pmatrix} 1 & c_0 \\ 1 & c_1 \end{pmatrix}, v(x) = \begin{pmatrix} W(x) \\ F(x) \end{pmatrix}$$

Due to the underlying physical effects, the phase at the first echo time $\varphi(x)$ and the phase evolution $\phi(x)$ vary continuously. In particular, they exhibit a smaller variation as a function of location than the MR data themselves.

In the following, techniques are explained that enable a determination of the first and second spectral components $W(x)$, $F(x)$ on the basis of the spectral model, i.e. on the basis of Equations (1)-(3). However, the fundamentals of the MR system that can be used for the MR measurement are initially explained with reference to FIG. 1.

In FIG. 1, an MR system 100 is shown that is designed to implement techniques, methods and steps according to the invention. The MR system 100 has a basic field magnet 110 that defines a tube 111. The magnet 110 generates the basic magnetic field parallel to its longitudinal axis. The basic magnetic field can exhibit inhomogeneities, thus local deviations from a desired value. An examination subject (here an examined person 101) can be slid on a bed table 102 into the magnet 110. Furthermore, the MR system 100 has a gradient system 140 to generate gradient fields that are used for MR imaging and for spatial coding of acquired raw data. The gradient system 140 typically has at least three gradient coils 141 that are separately controllable and positioned with good definition relative to one another. The gradient coils 141 enable gradient fields to be applied and switched along defined spatial directions (gradient axes). Switching the gradient fields can cause eddy current effects that, in turn, produce local magnetic fields. The gradient fields can be used for slice selection, for frequency coding (in the readout direction) and for phase coding, for example. A spatial coding of the raw data can thereby be achieved. The spatial directions that are respectively parallel to slice selection gradient fields, phase coding gradient fields and readout gradient fields do not necessarily need to be coincident with the machine coordinate system. Rather, they can be defined in relation to a k-space trajectory (for example), which can in turn be established on the basis of specific requirements of the respective MR measurement sequence and/or can be established based on anatomical properties of the examined person 101.

To deflect the nuclear spins from the polarization or alignment of their magnetization in the longitudinal direction that results in the basic magnetic field, an RF coil arrangement 121 is provided that radiates an amplitude-modulated RF excitation pulse in the examined person 101. A transverse magnetization of the nuclear spins can thereby be generated. To generate such RF excitation pulses, an RF transmission unit 131 is connected via an RF switch 130 with the RF coil arrangement 121. The RF transmission unit 131 can include an RF generator and an RF amplitude modulation unit. The RF excitation pulses deflect (flip) the transverse magnetization in 1D (slice-selectively) or 2D/3D (spatially selectively or globally) out of the steady state.

Furthermore, an RF acquisition unit 132 is coupled via the RF switch 130 with the RF coil arrangement 121. Via the RF acquisition unit 132, MR signals of the relaxing transverse magnetization (for example due to inductive injection into the RF coil arrangement 121) can be acquired as MR data.

In general, it is possible to use separate RF coil arrangements 121 for the radiation of the RF excitation pulses by means of the RF transmission unit 131 and for the acquisition of the MR data by means of the RF acquisition unit 132. For example, a volume coil 121 can be used for the radiation of RF pulses and a surface coil (not shown) which can be an array of RF coils can be used for the acquisition of raw data. For example, the surface coil can have 32 individual RF coils for the acquisition of the raw data, and therefore can be particularly suitable for partially parallel imaging (PPA, partially parallel acquisition). Suitable techniques are known to those skilled in the art and thus need not be explained herein.

The MR system 100 furthermore has an operating unit 150 that, for example, can include a monitor, a keyboard, a mouse, etc. User entries can be detected, and outputs to the user can be implemented by the operating unit 150. For example, via the operating unit 150 it is possible for individual operating modes or operating parameters of the MR system to be set by the user and/or automatically and/or by remote control.

Furthermore, the MR system 100 has a computer 160. For example, the computer 160 can be configured to implement diverse computation operations within the scope of the determination of the fat component and the water component. For example, the computer 160 can be configured in order to implement a numerical optimization and/or to process MR data with a Fourier transformation.

Figure 2:
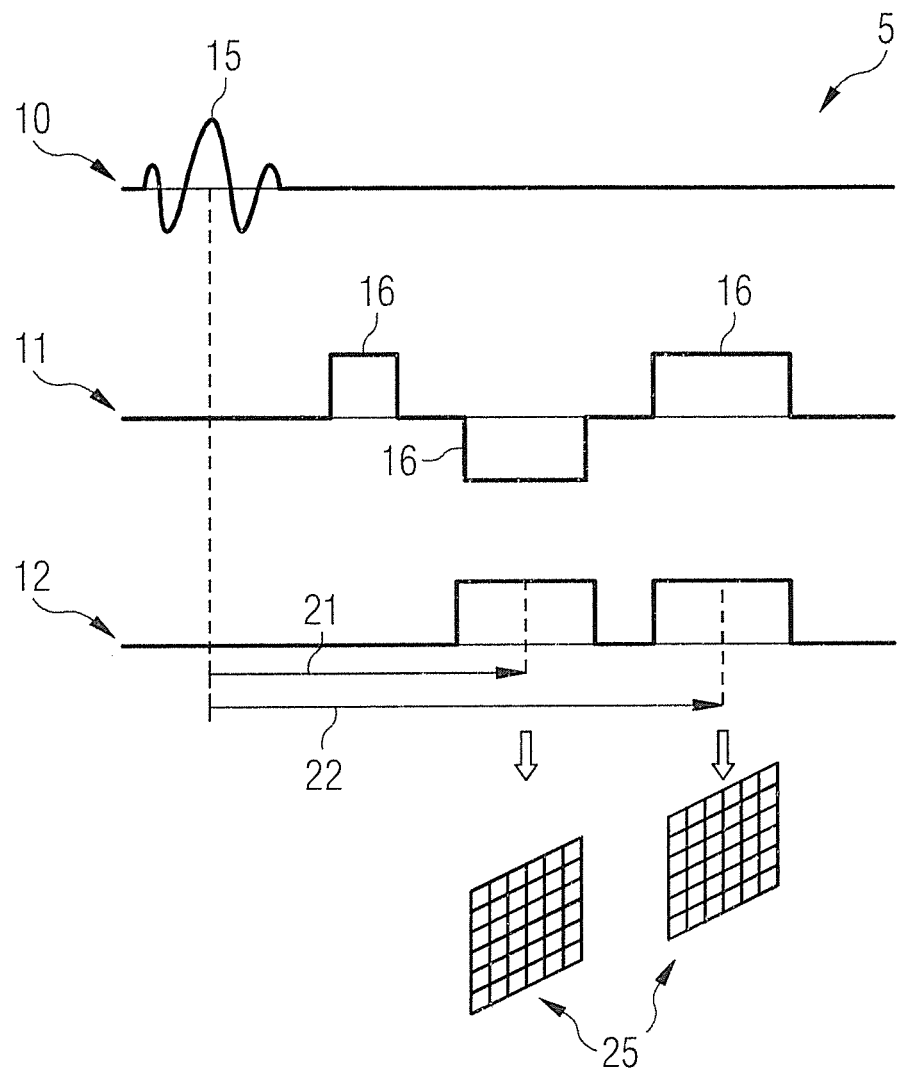
FIG. 2 shows a gradient echo MR measurement sequence in which two MR signals are acquired in a bipolar manner as MR data, respectively at a first echo time and at a second echo time.

In FIG. 2, a two-point Dixon gradient echo MR measurement sequence 5 is shown. A radio-frequency axis 10, a gradient field component 11 and a readout channel 12 are shown. An RF excitation pulse 15 is initially radiated. Readout gradient fields 16 are subsequently switched that form two gradient echoes at the first echo time 21 and the second echo time 22. The MR data 25—namely one MR signal at each echo times 21, 22—are received by the analog/digital converter, graphically indicated by the measurement blocks on the readout channel 12. The first and second echo times 21, 22 are defined in relation to a point in time known as the isodelay point in time of the RF excitation pulse 15 which, for example, lies approximately in the middle of the RF excitation pulse with a sinc amplitude envelope. Other definitions of the first and second echo times 21, 22 are possible and do not need to be discussed in detail in this context.

FIG. 2 is a simplified presentation since at least one slice selection gradient field and one phase coding gradient field (which are typically required for complete spatial coding of an image point of the MR data 25) are not shown. However, the MR data 25 are obtained with resolution for different image points (illustrated by the grid in FIG. 2), such that the additional gradient fields are also typically used for spatial coding.

Figure 3:
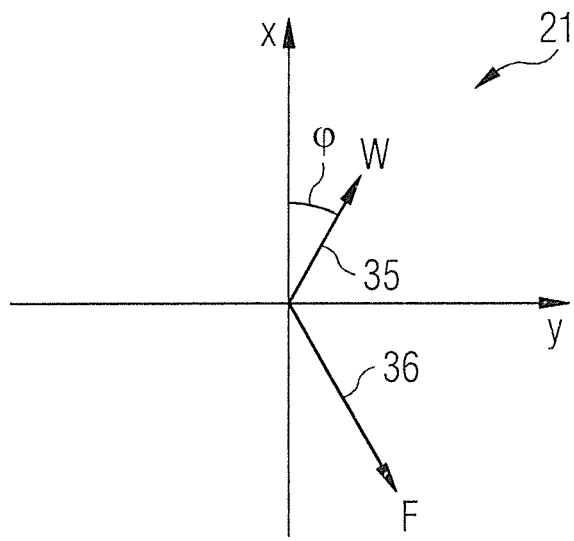
FIG. 3 illustrates a phase at the first echo time.

Although a gradient echo MR measurement sequence is shown in FIG. 2, other two-point Dixon MR measurement sequences can also be used. For example, a spin echo MR measurement sequence could be used, or a monopolar gradient echo MR measurement sequence The RF excitation pulse 15 deflects the magnetization out of its steady state along the longitudinal direction, such that what is known as a transverse component is created. The transversal component is typically depicted in the x-y plane (see FIGS. 3 and 4). In FIG. 3, the phase position of the water component 35 and of the fat component 36 at the first echo time 21 is shown. In particular, in FIG. 3 a situation is shown in which the MR measurement sequence 5 is adjusted to the water component 35. As can be seen from FIG. 3, the water component 35 has a phase $\varphi$ relative to a zero degree position (defined as a reference) along the x-axis. Due to the frequency shift between the water component 35 and the fat component 36, the fat component 36 has a different phase position than the water component 35.

Figure 4:
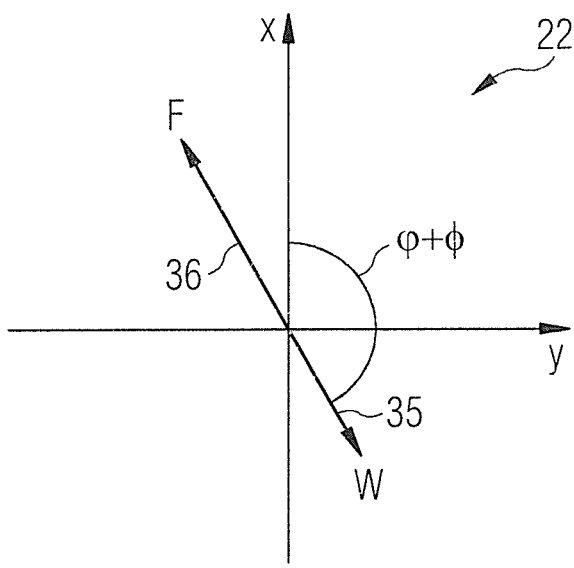
FIG. 4 illustrates a phase evolution between the first and second echo times.

In FIG. 4, the phase position of the water component 35 and of the fat component 36 at the second echo time 22 is shown. Now the water component 35 has a phase shift relative to the zero degree position (defined as a reference phase) along the x-axis of $\varphi+\phi$. The phase evolution $\phi$ thus designates an additionally acquired phase between the first and second echo times 21, 22 that, for example, is due to the field inhomogeneities and/or the eddy current effects.

As is explained above with regard to Equations (1)-(3), the spectral model can take into account this phase $\varphi$ at the first echo time 21 and the phase evolution $\phi$ between the first and second echo times 21, 22. It is now possible for an equation on the basis of which a numerical optimization to be implemented to determine the phase $\varphi$ at the first echo time 21 and/or the phase evolution $\phi$ has no explicit dependency on the water component 35 and the fat component 36.

Alternatively or additionally, phase $\varphi$ at the first echo time 21 and/or the phase evolution $\phi$ can be assumed to be constant within a defined region. This is shown in FIG. 5. In FIG. 5, grid points 40 of a computation grid are represented with dashed lines. The image points 30 of the MR data 25 are also represented with solid lines in FIG. 5. As can be seen from FIG. 5, the computation grid is defined such that it is of lower resolution in comparison to the MR data 25, meaning that a grid point 40 is larger than an image point 30. Each grid point 40 encompasses a predetermined number of adjacent image points 30 of the MR data 25. In the case of FIG. 5, sixteen image points 30 are respectively encompassed given quadratic grid points 40. For example, within the scope of the determination of the computation grid, the number of adjacent image points 30 of the MR data 25 that are encompassed by a grid point 40 are established depending on a user input and/or depending on a machine parameter of the MR system 100.

In the following, techniques are presented in which it is assumed, within the scope of a numerical optimization, that the phase $\varphi$ at the first echo time 21 and/or the phase evolution $\varphi$ between the first and second echo times 21, 22 are respectively constant within a grid point 40 of the computation grid. The phase $\varphi$ at the first echo time and/or the phase evolution $\varphi$ can thus also be designated as constant in parts. The water component 35 and the fat component 36 thus can be determined in a simple manner.

The water component 35 and the fat component 36 are illustrated in FIG. 5 in a schematic manner for only a few image points 30 of the MR data 25. In general, however, it is possible to determine the water component 35 and the fat component 36 for all image points 30 of the MR data, for example to determine them individually.

For example, the numerical optimization can be a chi-square optimization, such that this equation (based on Equation (3)) has the following form:

$$x^2(\{\varphi(x)\}, \{\phi(x)\}, \{v(x)\}) = \sum_{x \in U}(D(x) - \Phi(x)Av(x))^T(D(x) - \Phi(x)Av(x)). \quad (4)$$

wherein U designates a grid point 4 of the computation grid. The equation 4 is bilinear with regard to the water component 35 and fat component 36. Therefore, these can be eliminated by means of what is known as variable projection.

In contrast to known reference implementations in which both the weighting W of the water component 35 and the weighting F of the fat component 36 are assumed to have complex values, the present approach has the advantage that it reduces the number of variables taken into account within the scope of the numerical optimization given use for two-point Dixon techniques. In the following, the difference relative to the aforementioned reference implementations is illustrated in detail.

If $A_R = \Re (A)$ and $A_I = \Im (A)$ are provided, (5)

$$v(x) = (A_R^T A_R + A_I^T A_I)^{-1} \Re (A^T \phi(x)^T D(x))$$

$$= (A_R^T A_R + A_I^T A_I)^{-1} (A_R^T A_I^T) \begin{pmatrix} \Re (\Phi(x)^T D(x)) \\ \Im (\Phi(x)^T D(x)) \end{pmatrix}$$

is obtained and $$x^2(\{\varphi(x)\}, \{\phi(x)\}) = \sum_{x \in U} \left( D(x)^T D(x) - (\Re (\Phi(x)^T D(x)) \Im (\Phi(x)^T D(x))) \right. \quad (6)$$

$$\left. \underbrace{\begin{pmatrix} A_R \\ A_I \end{pmatrix}(A_R^T A_R + A_I^T A_I)^{-1}(A_R^T A_I^T)}_{=B_R} \begin{pmatrix} \Re (\Phi(x)^T D(x)) \\ \Im (\Phi(x)^T D(x)) \end{pmatrix} \right)$$

The matrix $B_R$ has a real value, is symmetrical and 2nd-order, with eigenvalues of 1, and represents a projection onto the space that is spanned by the columns $(A_R, A_I)^T$.

Therefore $B_R = \sum_{j=1,2} \tilde{w}_j \tilde{w}_j^T$ applies, wherein the vectors $\tilde{w}_j = (w_{R,j} + w + w_{I,j})^T$ are real-valued and orthonormal. If $u_j = w_{R,j} + i w_{I,j}$ is defined, $$x^2(\{\varphi(x)\}, \{\phi(x)\}) = \sum_{x \in U} \left( D(x)^T D(x) - \sum_{j=1,2} |\Re (u_j^T \Phi(x)^T D(x))|^2 \right) \quad (7)$$

is obtained.

The difference relative to the aforementioned complex-valued approach according to various reference implementations can be displayed using Equation (7). In the various reference implementations that are based on complex-valued weightings W, F it is not necessary to establish the real part as above in Equation (7). The eigenvalues $u_j$ can differ depending on the imaginary part $A_I$.

As can be seen from Equation 7, this has no explicit dependency on the water component 35 and the fat component 36. These were eliminated by means of the variable projection.

Equation (7) can be used as a basis for a numerical optimization in which the optimized phase $\varphi(x)$ at the first echo time 21 and the optimized phase evolution $\varphi(x)$ are determined. In other words: an optimization with regard to these two variables $\varphi(x), \varphi(x)$ can thus take place.

However, it is possible to simplify further, such that the phase $\varphi(x)$ at the first echo time 21 and/or the phase evolution $\varphi(x)$ are eliminated. The optimization can then respectively be implemented only with regard to the variable $\varphi(x), \varphi(x)$ that has not been eliminated.

This elimination is shown as an example for the phase $\varphi(x)$ at the first echo time 21, but corresponding techniques can also be directly applied for the eliminate of the phase evolution $\varphi(x)$. In other words, the equation taken into account within the numerical optimization can have no explicit dependency on the phase $\varphi$ at the first echo time 21 if only the phase evolution $\varphi$ is numerically optimized. Accordingly, the equation can have no explicit dependency on the phase evolution $\varphi$ if only the phase $\varphi$ at the first echo time 21 is numerically optimized. If the equation taken into account in the numerical optimization has no explicit dependency on the phase evolution $\varphi$, either it can be assumed that the phase $\varphi$ at the first echo time 21 varies within a grid point 40 of the computation grid or it can be assumed that the phase $\varphi$ at the first echo time 21 is constant within a grid point 40 of the computation grid. Accordingly, it analogously applies for the case that the equation has no explicit dependency on the phase 9 at the first echo time 21.

The latter case is illustrated in the following, wherein corresponding techniques can be directly applied to the elimination of the phase evolution $\varphi$. It can thus be selected whether the phase $\varphi$ at the first echo time 21 has a lower resolution than the MR data 25 (i.e. is constant within a grid point 40) or has a high resolution (i.e. has the same resolution as the MR data 25). For the two options it is respectively defined: $x_\varphi^2(\{\varphi(x)\})$ and $x_{\varphi(x)}^2(\{\varphi(x)\})$.

In both cases, the optimization problem is of the form:

$$\min_\alpha \left(-\Sigma_j (\Re(c_j e^{i\alpha}))^2\right) = -\frac{1}{2}\Sigma_j |c_j|^2 - \max_\alpha \left(\frac{1}{4}\Sigma_j(c_j^2 e^{2i\alpha} + c_j^{*2} e^{-2i\alpha})\right) \quad (8)$$

$$= -\frac{1}{2}\Sigma_j |c_j|^2 - \frac{1}{2}\left|\Sigma_j c_j^2\right|,$$

wherein $e^{i\alpha} = |\Sigma_j c_j^2|^{1/2}/(\Sigma_j c_j^2)^{1/2}$. Due to the extraction of the root, there is an ambiguity in the algebraic sign that, for example, can be made unambiguous via the selection of the weighting W(x) of the fat component 36 in a positive value. This selection of the algebraic sign can then be limited: $\varphi \in [0, \pi)$ $$x_\varphi^2(\{\phi(x)\}) = \sum_{x \in U} D(x)^T D(x) - \quad (9)$$

$$\frac{1}{2}\sum_{x \in U}\sum_{j=1,2}\left|u_j^T \Psi(x)^T D(x)\right|^2 - \left|\sum_{x \in U}\sum_{j=1,2}(u_j^T \Psi(x)^T D(x))^2\right|$$

$$x_{\varphi(x)}^2(\{\phi(x)\}) = \sum_{x \in U}\left(D(x)^T D(x) - \right.$$

$$\left.\frac{1}{2}\sum_{j=1,2}|u_j^T \Psi(x)^T D(x)|^2 - \left|\sum_{j=1,2}(u_j^T \Psi(x)^T D(x))^2\right|\right)$$

is then obtained, where $\Psi(x) = e^{-i\varphi(x)}\Phi(x)$ has been defined. From a comparison of the two terms in Equation 9 it is apparent that the fact of whether $\varphi$ is assumed to be constant within a grid point 40 or not affects the position of the sum over the different image points 30 of the MR data 25.

In principle, an algebraic simplification of the aforementioned Equation 9 is not possible. If the phase evolution $\varphi$ is assumed to be constant within a grid point 40, $$x_\varphi^2(\phi) = \sum_{x \in U}\left(D(x)^T D(x) - \frac{1}{2}\sum_{j=1,2}(|u_{j,o}^T D_o(x)|)^2 + \left|u_{j,1}^T D_1(x)\right|^2\right) - \quad (10)$$

$$\frac{1}{2}\left(\sum_{x \in U}\sum_{j=1,2}(u_{j,0}^T D_0(x))(u_{j,1}^T D_1(x))^*\right)e^{-i\phi} -$$

$$\frac{1}{2}\left(\sum_{x \in U}\sum_{j=1,2}(u_{j,0}^T D_0(x))^*(u_{j,1}^T D_1(x))\right)e^{i\phi}$$

$$\left|\sum_{x \in U}\sum_{j=1,2}((u_{j,0}^T D_0(x))^2 + (u_{j,1}^T D_1(x))^2 e^{2i\phi} + \right.$$

$$2(u_{j,0}^T D_0(x))(u_{j,1}^T D_1(x))e^{i\phi})\bigg|$$

and $$x_{\varphi(x)}^2(\phi) = \sum_{x \in U}\left(D(x)^T D(x) - \frac{1}{2}\sum_{j=1,2}(|u_{j,o}^T D_o(x)|)^2 + \left|u_{j,1}^T D_1(x)\right|^2\right) -$$

$$\frac{1}{2}\left(\sum_{x \in U}\sum_{j=1,2}(u_{j,0}^T D_0(x))^*(u_{j,1}^T D_1(x))\right)e^{i\phi}$$

$$\sum_{x \in U}\left|\sum_{j=1,2}((u_{j,0}^T D_0(x))^2 + (u_{j,1}^T D_1(x))^2 e^{2i\phi} + \right.$$

$$2(u_{j,0}^\prime D_0(x))(u_{j,1}^T D_1(x))e^{i\phi})\bigg|$$

are obtained.

It can be shown that Equations (10) and (11) have at most two minima for $\varphi \in [0, 2\pi)$ but must be solved numerically. Equations (10) and (11) can thus be taken into account on the basis of the numerical optimization to determine the phase evolution $\varphi$. After obtaining the optimized phase evolution $\varphi$, the phase $\varphi$ at the first echo time 21 can then be determined analytically and the analytical calculation of the water component 35 and of the fat component 36 can take place. This analytical calculation can be based on a variable back-projection of the real-value weightings W, F of the water component 35 and the fat component 36.

In FIG. 6, a situation is shown in which the implementation of the first numerical optimization (here with regard to the phase evolution $\varphi$) provides two respective result candidates (labeled with stars in FIG. 6) for the image points 30-1, 30-2. In the scenario of FIG. 6, these image points 30-1, 30-2 are directly adjacent. The optimization can furthermore include the implementation of a region growing technique for the multiple image points 30-1, 30-2 of the MR data 25. For each image point 30-1, 30-2, a value can therefore be selected from the multiple result candidates as the optimized phase evolution $\varphi$. For example, after the smaller value of $\varphi$ has been identified as the actual value for the physically relevant solution for the image point 30-2, the smaller value of $\varphi$ could also be identified as the actual physically relevant solution for the image point 30-1 (respectively illustrated by an arrow and the vertical dashed lines in FIG. 6). In principle, region growing techniques are known to those skilled in the art in connection with the discovery of the relevant solution from multiple result candidates in connection with the optimization in Dixon techniques, such that no additional details need be explained herein.

A flowchart of a method according to various aspects of the present invention is shown in FIG. 7. The method begins in step S1. In step S2, the MR data 25 are initially acquired at the first echo time 21 and at the second echo time 22.

The determination unit of the computation grid then takes place in step S3. For example, within the scope of step S3 the number of image points 30 per grid point 40 can be established.

In step S4 a check is made as to whether the optimization should occur only in one variable, i.e. with regard to either the phase $\varphi$ at the first echo time 21 or with regard to the phase evolution $\varphi$, for example. If this is the case, in step S5 a check is made as to whether the numerical optimization should occur with regard to the phase $\varphi$ at the first echo time 21. If this is the case, in step S6 the chi-square optimization is implemented to determine the optimized phase $\varphi$ at the first echo time 21. The phase evolution $\varphi$ is subsequently determined analytically in step S7.

If it is established in step S5 that the optimization should not occur with regard to the phase $\varphi$ at the first echo time 21, in step S8 the implementation takes place in the numerical optimization to determine the optimized phase. The analytical determination of the phase $\varphi$ at the first echo time 21 subsequently takes place in step S9.

In contrast to this, if it is established in step S4 that the optimization should occur not only in one of the phase $\varphi$ at the first echo time 21 and the phase evolution $\varphi$, in step S10 the implementation of the chi-square optimization takes place both to determine the optimized phase $\varphi$ at the first echo time 21 and to determine the optimized phase evolution $\varphi$.

Independent of the output of the checks in step S4 and step S5, a value for both the phase $\varphi$ at the first echo time 21 and for the phase evolution $\varphi$ thus respectively exists after the steps S7, S9 or S10.

The determination of the fat component 35 and the water component 36 can then take place in step S11. The method ends in step S12.

Although modifications and changes may be suggested by those skilled in the art, it is the intention of the inventor to embody within the patent warranted hereon all changes and

I claim as my invention:

1. A method for acquiring magnetic resonance data from an examination subject, comprising:

operating a magnetic resonance data acquisition unit, that generates a basic magnetic field in which an examination subject is situated, according to a magnetic resonance data acquisition sequence in which magnetic resonance data are acquired from the examination subject at each of a first echo time and a second echo time that occur in said magnetic resonance data acquisition sequence, said magnetic resonance data acquired at each of said first echo time and said second echo time representing multiple image points of an image to be generated of the examination subject;

providing said magnetic resonance data to a computerized processor and, in said computerized processor, operating on said magnetic resonance data with a spectral model of a two-point Dixon technique that relates said magnetic resonance data to a first spectral component and a second spectral component of said magnetic resonance data, and a phase of said magnetic resonance data at said first echo time, and a phase evolution of said magnetic resonance data that occurs due to at least one of field inhomogeneities in said basic magnetic field and eddy currents that occur in said magnetic resonance data acquisition unit between said first echo time and said second echo time;

in said processor, computing a grid having a lower resolution than said image points, with each grid point of said grid encompassing a predetermined number of adjacent image points represented by said magnetic resonance data;

in said processor, for each image point of said magnetic resonance data, implementing a numerical optimization that determines an optimization result selected from the group consisting of an optimization of said phase at said first echo time and an optimization of said phase evolution, with said optimization being implemented based on an equation based on at least one of said phase at said first echo time and said phase evolution being constant for said image points that are encompassed by a grid point of said grid;

in said processor, analytically calculating said first spectral component and said second spectral component from said optimization result; and making the calculated first and second spectral components available in electronic form at an output of said processor in a format allowing reconstruction of an in-phase image and an out-of-phase image according to said two-point Dixon technique that is modeled by said spectral model.

2. A method as claimed in claim 1 comprising employing, as said equation, an equation having no explicit dependency on either of said first spectral component and said spectral component.

3. A method as claimed in claim 2 comprising employing, as said equation, an equation embodying a variable projection of real-value weightings of said first and second spectral components based on said spectral model.

4. A method as claimed in claim 1 comprising computing said grid by establishing a predetermined number of adjacent image points of said magnetic resonance data that are encompassed by a grid point, dependent on at least one of a user entry made into said computerized processor and a machine parameter of said magnetic resonance data acquisition unit.

5. A method as claimed in claim 1 comprising numerically optimizing only said phase evolution, and using, as said equation, an equation embodying a variation of said phase at said first echo time that occurs for image points that are encompassed by a grid point of said grid.

6. A method as claimed in claim 1 comprising numerically optimizing only said phase at said first echo time, and using, as said equation, an equation embodying a variation of said phase evolution that occurs for image points that are encompassed by a grid point of said grid.

7. A method as claimed in claim 1 comprising analytically calculating said first spectral component and said second spectral component by interpolating at least one of the phase at said first echo time and said phase evolution between adjacent grid points, and determining said first and second spectral components based on said one of the interpolated phase at the first echo time and the interpolated phase evolution between adjacent grid points.

8. A method as claimed in claim 1 comprising optimizing only said phase evolution between adjacent grid points and using, as said equation, an equation having no explicit dependency on said phase at said first echo time.

9. A method as claimed in claim 1 comprising numerically optimizing only said phase at said first echo time and using, as said equation, an equation having no explicit dependency on said phase evolution.

10. A method as claimed in claim 1 comprising analytically calculating said first spectral component and said second spectral component using a variable back-projection of real-value weightings of said first and second spectral components in said spectral model.

11. A method as claimed in claim 1 wherein said optimization result comprises a preliminary optimization result comprising multiple result candidates, and wherein said numerical optimization comprises implementing a region growing technique for said multiple image points of said magnetic resonance data to select a value, from said multiple result candidates, to be used as said optimization result.

12. A method as claimed in claim 1 comprising implementing said numerical optimization as a chi-square optimization.

13. A method for acquiring magnetic resonance data from an examination subject, comprising:

operating a magnetic resonance data acquisition unit, that generates a basic magnetic field in which an examination subject is situated, according to a magnetic resonance data acquisition sequence in which magnetic resonance data are acquired from the examination subject at each of a first echo time and a second echo time that occur in said magnetic resonance data acquisition sequence, said magnetic resonance data acquired at each of said first echo time and said second echo time representing multiple image points of an image to be generated of the examination subject;

providing said magnetic resonance data to a computerized processor and, in said computerized processor, operating on said magnetic resonance data with a spectral model of a two-point Dixon technique that relates said magnetic resonance data to a first spectral component and a second spectral component of said magnetic resonance data, and a phase of said magnetic resonance data at said first echo time, and a phase evolution of said magnetic resonance data that occurs due to at least one of field inhomogeneities in said basic magnetic field and eddy currents that occur in said magnetic resonance data acquisition unit between said first echo time and said second echo time;

in said processor, for each image point of said magnetic resonance data, implementing a numerical optimization that determines an optimization result selected from the group consisting of an optimization of said phase at said first echo time and an optimization of said phase evolution, using an equation having no explicit dependency on either of said first spectral component and said second spectral component;

in said processor, analytically calculating said first spectral component and said second spectral component from said optimization result; and making the calculated first and second spectral components available in electronic form at an output of said processor in a format allowing reconstruction of an in-phase image and an out-of-phase image according to said two-point Dixon technique that is modeled by said spectral model.

14. A method as claimed in claim 13 comprising optimizing only said phase evolution between adjacent grid points and using, as said equation, an equation having no explicit dependency on said phase at said first echo time.

15. A method as claimed in claim 13 comprising numerically optimizing only said phase at said first echo time and using, as said equation, an equation having no explicit dependency on said phase evolution.

16. A method as claimed in claim 13 comprising analytically calculating said first spectral component and said second spectral component using a variable back-projection of real-value weightings of said first and second spectral components in said spectral model.

17. A method as claimed in claim 13 wherein said optimization result comprises a preliminary optimization result comprising multiple result candidates, and wherein said numerical optimization comprises implementing a region growing technique for said multiple image points of said magnetic resonance data to select a value, from said multiple result candidates, to be used as said optimization result.

18. A method as claimed in claim 13 comprising implementing said numerical optimization as a chi-square optimization.

19. An apparatus for acquiring magnetic resonance data from an examination subject, comprising:

a magnetic resonance data acquisition unit that generates a basic magnetic field in which an examination subject is situated;

a control computer configured to operate said data acquisition unit according to a magnetic resonance data acquisition sequence in which magnetic resonance data are acquired from the examination subject at each of a first echo time and a second echo time that occur in said magnetic resonance data acquisition sequence, said magnetic resonance data acquired at each of said first echo time and said second echo time representing multiple image points of an image to be generated of the examination subject;

a computerized processor provided with said magnetic resonance data, said computerized processor being configured to operate on said magnetic resonance data with a spectral model of a two-point Dixon technique that relates said magnetic resonance data to a first spectral component and a second spectral component of said magnetic resonance data, and a phase of said magnetic resonance data at said first echo time, and a phase evolution of said magnetic resonance data that occurs due to at least one of field inhomogeneities in said basic magnetic field and eddy currents that occur in said magnetic resonance data acquisition unit between said first echo time and said second echo time;

said processor being configured to compute a grid having a lower resolution than said image points, with each grid point of said grid encompassing a predetermined number of adjacent image points represented by said magnetic resonance data;

said processor being configured to implement, for each image point of said magnetic resonance data, a numerical optimization that determines an optimization result selected from the group consisting of an optimization of said phase at said first echo time and an optimization of said phase evolution, with said optimization being implemented based on an equation based on at least one of said phase at said first echo time and said phase evolution being constant for said image points that are encompassed by a grid point of said grid;

said processor being configured to analytically calculate said first spectral component and said second spectral component from said optimization result; and said processor being configured to make the calculated first and second spectral components available in electronic form at an output of said processor in a format allowing reconstruction of an in-phase image and an out-of-phase image according to said two-point Dixon technique that is modeled by said spectral model.

20. An apparatus for acquiring magnetic resonance data from an examination subject, comprising:

operating a magnetic resonance data acquisition unit that generates a basic magnetic field in which an examination subject is situated;

a control computer configured to operate said data acquisition unit, according to a magnetic resonance data acquisition sequence in which magnetic resonance data are acquired from the examination subject at each of a first echo time and a second echo time that occur in said magnetic resonance data acquisition sequence, said magnetic resonance data acquired at each of said first echo time and said second echo time representing multiple image points of an image to be generated of the examination subject;

a computerized processor provided with said magnetic resonance data, said computerized processor being configured to operate on said magnetic resonance data with a spectral model of a two-point Dixon technique that relates said magnetic resonance data to a first spectral component and a second spectral component of said magnetic resonance data, and a phase of said magnetic resonance data at said first echo time, and a phase evolution of said magnetic resonance data that occurs due to at least one of field inhomogeneities in said basic magnetic field and eddy currents that occur in said magnetic resonance data acquisition unit between said first echo time and said second echo time;

said processor being configured to implement, for each image point of said magnetic resonance data, a numerical optimization that determines an optimization result selected from the group consisting of an optimization of said phase at said first echo time and an optimization of said phase evolution, using an equation having no explicit dependency on either of said first spectral component and said second spectral component;

said processor being configured to analytically calculate said first spectral component and said second spectral component from said optimization result; and said computerized processor being configured to make the calculated first and second spectral components available in electronic form at an output of said processor in a format allowing reconstruction of an in-phase image and an out-of-phase image according to said two-point Dixon technique that is modeled by said spectral model.

* * * * *